United States Patent
Beck

(10) Patent No.: US 8,823,869 B2
(45) Date of Patent: Sep. 2, 2014

(54) METHOD AND APPARATUS FOR OPTICALLY INSPECTING A TEST SPECIMEN HAVING AN AT LEAST PARTLY REFLECTIVE SURFACE

(75) Inventor: Rolf Beck, Esslingen (DE)

(73) Assignee: Carl Zeiss OIM GmbH, Wangen (DE)

( * ) Notice: Subject to any disclaimer, the term of this patent is extended or adjusted under 35 U.S.C. 154(b) by 0 days.

(21) Appl. No.: 13/565,375

(22) Filed: Aug. 2, 2012

(65) Prior Publication Data

US 2012/0327295 A1 Dec. 27, 2012

Related U.S. Application Data

(63) Continuation of application No. PCT/EP2011/000459, filed on Feb. 1, 2011.

(30) Foreign Application Priority Data

Feb. 3, 2010 (DE) .......................... 10 2010 007 396

(51) Int. Cl.
| | |
|---|---|
| H04N 5/222 | (2006.01) |
| G01N 21/55 | (2014.01) |
| H04N 7/18 | (2006.01) |
| H04N 5/225 | (2006.01) |
| G01B 11/25 | (2006.01) |
| G01N 21/47 | (2006.01) |
| G01B 11/245 | (2006.01) |
| G01N 21/88 | (2006.01) |

(52) U.S. Cl.
CPC ......... *G01N 21/4738* (2013.01); *H04N 5/2256* (2013.01); *G01N 2021/8829* (2013.01); *G01B 11/2527* (2013.01); *G01N 21/8851* (2013.01); *G01N 21/8806* (2013.01); *H04N 7/18* (2013.01); *G01B 11/25* (2013.01); *G01B 11/245* (2013.01)
USPC ............................ 348/370; 356/445; 348/125

(58) Field of Classification Search
CPC ..... H04N 7/18; H04N 5/2256; G01B 11/245; G01B 11/25; G01B 11/2527; G01N 2021/8829; G01N 21/4738; G01N 21/8806; G01N 21/8851

USPC .......... 348/370–371, 125–134; 356/445–448, 356/600
See application file for complete search history.

(56) References Cited

U.S. PATENT DOCUMENTS 4,755,058 A * 7/1988 Shaffer .......................... 356/408
7,360,899 B2 * 4/2008 McGuire et al. ................ 353/20
(Continued)

FOREIGN PATENT DOCUMENTS

| DE | 198 21 059 A1 | 12/1999 |
|---|---|---|
| DE | 102 58 130 A1 | 6/2004 |

(Continued)

OTHER PUBLICATIONS

Hoefling et al, "Phase reflection-a new solution for the detection of shape defects on car body sheets", Opt. Eng. Jan. 2000, pp. 175 to 182, 39(1), XP-002638174.
International Search Report dated May 20, 2011 of international application PCT/EP 2011/000459 on which this application is based.

* cited by examiner

Primary Examiner — Aung S Moe
Assistant Examiner — Amy Hsu
(74) Attorney, Agent, or Firm — Walter Ottesen P.A.

(57) ABSTRACT

An apparatus for optically inspecting a test specimen has an at least partly reflective surface including a camera having a number of pixels and an illumination device having a multiplicity of spatially distributed light sources. A workpiece receptacle serves for positioning the test specimen relative to the illumination device and the camera, such that light from the light sources is reflected by the surface to the camera. An evaluation and control unit generates a series of different illumination patterns on the surface, wherein in the course of the series different light sources are switched on. An individual light origin region is determined on the basis of the images recorded by the camera for at least one pixel, whereby the region represents a spatial distribution of individual light contributions generated by the light sources via the surface on the at least one pixel.

13 Claims, 2 Drawing Sheets

(56) References Cited

U.S. PATENT DOCUMENTS

| | | | |
|---|---|---|---|
| 7,649,628 B2 * | 1/2010 | Wadman | 356/445 |
| 2004/0021771 A1 * | 2/2004 | Stearns et al. | 348/131 |
| 2006/0139575 A1 * | 6/2006 | Alasaarela et al. | 353/31 |
| 2010/0128221 A1 * | 5/2010 | Muller et al. | 351/207 |
| 2011/0090316 A1 * | 4/2011 | Stearns et al. | 348/46 |

FOREIGN PATENT DOCUMENTS

| | | |
|---|---|---|
| DE | 10 2007 063 529 A1 | 7/2009 |
| JP | 2007-183225 A | 7/2007 |
| WO | WO 2005/031251 A1 | 4/2005 |

METHOD AND APPARATUS FOR OPTICALLY INSPECTING A TEST SPECIMEN HAVING AN AT LEAST PARTLY REFLECTIVE SURFACE

CROSS REFERENCE TO RELATED APPLICATIONS

This application is a continuation application of international patent application PCT/EP 2011/000459, filed Feb. 1, 2011, designating the United States and claiming priority from German application 10 2010 007 396.2, filed Feb. 3, 2010, and the entire content of both applications is incorporated herein by reference.

FIELD OF THE INVENTION

The present invention relates to a method for optically inspecting a test specimen having an at least partly reflective surface, comprising the following steps:
providing a camera having a number of pixels,
providing an illumination device having a multiplicity of spatially distributed light sources,
positioning the test specimen relative to the illumination device and the camera, such that light from the light sources is reflected via the surface to the camera,
generating a series of different illumination patterns on the surface, wherein different light sources are switched on in the course of the series,
recording a series of images of the surface with in each case one of the illumination patterns, and
determining properties of the test specimen in a manner dependent on the images.

The invention furthermore relates to an apparatus for optically inspecting a test specimen having an at least partly reflective surface, comprising a camera having a number of pixels, comprising an illumination device having a multiplicity of spatially distributed light sources, comprising a workpiece receptacle for positioning the test specimen relative to the illumination device and the camera, such that light from the light sources is reflected via the surface to the camera, comprising a control unit for generating a series of different illumination patterns on the surface, wherein different light sources are switched on in the course of the series, and for recording a series of images of the surface with in each case one of the illumination patterns, and comprising an evaluation unit for determining properties of the test specimen in a manner dependent on the images.

BACKGROUND OF THE INVENTION

Such a method and such an apparatus are known from DE 10 2007 063 529 A1, for example.

The known method and the known apparatus use a multiplicity of different illumination patterns each having a spatial intensity profile having a defined period. In preferred exemplary embodiments, the illumination patterns are bright and dark stripes which form a sinusoidal intensity profile transversely with respect to the stripe direction. If such a pattern is displaced relative to the surface of a test specimen and if at least three images of the surface are recorded with the displaced stripe patterns, on the basis of the recorded images it is possible to determine different properties of the surface, in particular the local inclination of each surface point considered or a local scattering behavior of the surface point. However, the known method presupposes that the reflection properties of the surface examined allow a sufficiently distinct separation of the bright and dark stripes in the recorded images. The narrower the individual stripes of the illumination pattern, the more likely the stripes "blur" in the recorded images if the surface scatters diffusely. On the other hand, narrow stripes (corresponding to short periods of the intensity profile) enable a higher resolution and a higher measurement accuracy. For this reason, DE 10 2007 063 529 A1 proposes using a plurality of illumination patterns having intensity profiles having different periods in order to determine an optimum stripe width (period) in this way. In other words, the known method and the known apparatus use a multiplicity of illumination patterns having spatial intensity profiles having different periods in order to obtain a characteristic variable that is representative of the scattering characteristic of the surface examined.

The method described in DE 10 2007 063 529 A1 and the corresponding apparatus enable automated inspection of a test specimen having an at least partly reflective surface, wherein the prior knowledge about the properties of the test specimen that is required for the inspection can be reduced by comparison with even older methods. However, the known method and the known apparatus are still not optimal, since the stripe direction also influences the detection capability of the method and of the apparatus. Moreover, at least three (preferably at least four) images of the surfaces have to be recorded for each stripe width (period) and for each stripe direction, wherein the surface is displaced relative to the stripe patterns in each image. In the case of an unknown surface or a surface which can be characterized only with difficulty in advance, a high number of image recordings and shift steps are therefore required.

Nevertheless, the known method and the known apparatus do not yield complete characterization of an unknown surface, unless each surface point were recorded with a large number of illumination patterns with finely gradated stripe widths, stripe directions and shift positions.

WO 2005/031251 A1 discloses a similar method and a similar apparatus. The document also proposes the use of illumination patterns having different stripe periods in order, inter alia, to determine the reflectivity of the surface of a test specimen. With regard to the disadvantages, the same statements as those made in respect of the method and the apparatus from DE 10 2007 063 529 A1 are applicable.

There are a number of further known methods for inspecting a test specimen, wherein the test specimen is recorded together with a defined illumination pattern and the resulting images are evaluated. They include in particular stripe projection methods, wherein a stripe pattern is projected from a known position onto the surface of the test specimen in order to determine shape features of the test specimen on the basis of trigonometrical relationships. Furthermore, one method is known as Shape from Shading. This is a method wherein a test specimen is illuminated from different directions without changing its position relative to the camera, wherein shape features of the test specimen are determined on the basis of the different brightnesses depending on the light incidence direction. However, stripe projection and Shape from Shading are not suitable, or are suitable only to a limited extent, for test specimens having a highly lustrous surface. Furthermore, they do not yield a characterization of the test specimen surface, but rather only shape features.

SUMMARY OF THE INVENTION

Against this background, it is an object of the present invention to specify a method and an apparatus of the type mentioned in the introduction which enable the most comprehensive possible metrological characterization and/or type classification of a test specimen having an at least partly reflective surface.

In accordance with a first aspect of the present invention this object is achieved by means of a method of the type mentioned in the introduction wherein an individual light origin region is determined on the basis of the images for at least one pixel, the region representing a spatial distribution of (preferably all) individual light contributions generated by the light sources via the surface on the at least one pixel, wherein the properties of the test specimen are determined on the basis of the individual light origin region.

In accordance with a further aspect of the invention, this object is achieved by means of an apparatus of the type mentioned in the introduction wherein the evaluation unit is firstly designed to determine an individual light origin region on the basis of the images for at least one pixel, the region representing a spatial distribution of individual light contributions generated by the light sources used via the surface on the at least one pixel, and wherein the evaluation unit is furthermore designed to determine the properties of the test specimen on the basis of the individual light origin region.

The novel method and the novel apparatus are based on the concept of determining the scattering characteristic of a point on the test specimen surface by examining which of the spatially distributed light sources a defined camera pixel can "see" via the test specimen surface at the relevant surface point. Each light source which the camera pixel can "see" via the surface point can generate a light contribution on the camera pixel. The light contribution depends on the position of the light source, the position of the camera pixel and the scattering characteristic of the surface point. If a highly specularly reflective surface is involved, the law "angle of incidence=angle of reflection" is substantially applicable. The defined camera pixel will therefore be able to "see" only a small number of light sources. The light origin region for the defined pixel is relatively small. By contrast, a diffusely scattering surface "distributes" incident light into a larger solid angle. Accordingly, even light sources which are situated further away and which cannot reach the defined pixel according to the law "angle of incidence=angle of reflection" can nevertheless generate a light contribution on the camera pixel.

The novel method and the novel apparatus utilize this relationship in order to characterize the scattering characteristic of a surface point of the test specimen surface on the basis of the spatial directions from which light can reach a defined measurement point, namely the defined camera pixel. The set of these spatial directions defines the light origin region, which could alternatively also be designated as the light gathering region or light collecting region of a specific camera pixel.

The light origin region enables a comprehensive characterization of the scattering properties of a surface point considered. On the basis of parameters such as shape, extent, orientation and/or symmetry of the light origin region, the scattering properties of the surface point can be characterized in a simple and reproducible manner. If the light origin region is determined for a multiplicity of camera pixels, a location-dependent characterization of the scattering properties of the surface is obtained.

The reproducible determination of the light origin region enables a simple and rapidly comparable type classification of test specimens having largely unknown surface properties. At the same time, the novel method and the novel apparatus require very little prior knowledge about the properties of the test specimen. The abovementioned object is therefore completely achieved.

In one preferred configuration of the invention, in the course of the series each light source whose light is reflected via the surface to the camera is switched on once.

This configuration makes it possible to determine the individual light origin region very accurately, and it therefore contributes to a comprehensive characterization of the test specimen surface. In principle, it suffices for each light source whose light is or can be reflected via the surface to the camera to be switched on exactly once in order to determine the individual light contribution of these light sources. In some exemplary embodiments, this variant is also preferred in order to reduce the number of image recordings. However, it is also possible for light sources to be switched on multiple times in the course of the novel method, for instance in order to be able to reduce statistical influences by averaging. Furthermore, it is possible, in principle, for each light source present to be switched on (at least) once in order to determine the individual light origin region of a pixel. This is advantageous particularly if the reflection properties of the test specimen are unknown. Alternatively, it is possible for light sources whose light cannot reach the camera via the test specimen surface per se to be left unused or disregarded on account of corresponding a priori knowledge.

In a further configuration, in the course of the series each light source whose light is reflected via the surface to the camera is switched on individually. In this case, it is particularly preferred if the individual light sources are point light sources. In other exemplary embodiments, however, the light sources in this configuration can be linear light sources that each generate a "light line".

This configuration enables the light sources to be driven in a very simple manner. Moreover, it is possible to determine the individual light origin region for a multiplicity of pixels by simply combining the images recorded in the course of the series. In one exemplary embodiment, for each camera pixel considered, all images which generate a light contribution on the pixel considered are grouped together. A data set representing an individual light contribution in a manner dependent on the location of the individual light sources is thus obtained for each camera pixel considered. A further advantage of this configuration is that the individual light sources have only little time to heat up, with the result that thermal problems are avoided. Overall, this configuration enables a simple and cost-effective realization of the novel apparatus.

In a further configuration, in the course of the series a plurality of light sources are switched on simultaneously in order to generate a multiplicity of spatially extended illumination patterns, wherein the individual light contributions of the light sources used are calculated on the basis of the multiplicity of spatially extended illumination patterns.

In principle, it is possible to determine an individual light contribution of all light sources used even when a plurality of light sources are switched on simultaneously. In the simplest case, light sources whose light contributions only reach different pixels can be switched on simultaneously. For the individual pixels, this situation is identical to the alternative configuration wherein each light source is switched on individually. However, it is also possible to determine individual light contributions if a plurality of light sources simultaneously make a light contribution to a specific pixel. By way of example, the extended illumination patterns can form a (two-dimensional, areally extended) Fourier series from which the light contributions of the individual light sources can be calculated by a mathematical Fourier transformation.

This corresponds to the decomposition of a Dirac impulse into a Fourier series. Extended illumination patterns having a large spatial bandwidth and an individual peak as autocorrelation function are generally suitable. These include, for example, binary Pseudo Random Noise (PRN) sequences or so-called chirp patterns. A chirp is a sinusoidal oscillation having a linearly varied frequency. Therefore, a two-dimensional illumination pattern corresponding to the Fresnel zone plate is particularly advantageous. If it were desired to analyze the scattering characteristic of the test specimen surface only in one viewing direction, illumination patterns having parallel light lines which are switched on individually are suitable, in principle. If an illumination device having a multiplicity of point light sources is used, such light lines can be generated in a simple manner by point light sources situated along the desired line being switched on simultaneously. Finally, the individual light contributions of the light sources used can also be determined on the basis of spatially extended illumination patterns by calculating the "centroid" of the illumination patterns used from the point of view of the defined pixel. All these variants enable image acquisition with a reduced number of images. The "price" is the required computational complexity or the restriction of the information obtained to one test specimen axis. Given corresponding computing capacity, however, apparatuses that operate very fast can be realized with this configuration.

In a further configuration, the light sources are each digitally switched on or off in the course of the series.

In this configuration, the individual light sources are switched on with a defined brightness that is largely identical for all the light sources, if they are required for generating the illumination patterns. Alternatively, in other configurations it is possible to switch on the individual light sources with a variable brightness lying between the "extreme values" (off and on with maximum/defined brightness) in accordance with the configuration preferred here. This last is advantageous in order to generate illumination patterns having sinusoidal intensity profiles. However, "digitally" switching the individual light source on/off enables higher contrasts and a better signal/noise ratio in the recorded images, which is advantageous for the determination of the individual light origin regions.

In a further configuration, region properties of the individual light origin region are identified, wherein the properties of the test specimen are determined in a manner dependent on the region properties of the individual light origin region.

In this configuration, the test specimen is characterized on the basis of region properties of the individual light origin region. It is particularly advantageous if the identified region properties represent at least one of the following region properties: shape of the individual light origin region, extent of the individual light origin region, symmetry of the individual light origin region, orientation of the individual light origin region, intensity distribution within the individual light origin region. As has already been mentioned further above, the extent of the individual light origin region can be a qualitative feature which characterizes the width of the scattering lobe of the test specimen surface at the surface point considered. An extended light origin region indicates a rather diffusely scattering surface, while a narrowly delimited light origin region indicates a highly reflective surface. The position and orientation of the light origin region and the symmetry thereof also characterize the scattering properties of the test specimen surface. The intensity distribution within the individual light origin region furthermore also supplies information regarding the magnitude of the light contributions of the individual "visible" light sources (from the point of view of the defined camera pixel). The use of such region properties enables a simple type classification of the test specimen surface on the basis of a small number of parameters. In this case, the preferred region properties represent valuable information about the test specimen surface. Thus, a highly asymmetrical light origin region, for instance, indicates that the reflection properties of the test specimen surface are greatly dependent on the viewing direction, which allows conclusions to be drawn about material properties of the test specimen surface, for instance about turning grooves, milling grooves or other direction-dependent processing traces.

In a further configuration, a defined number of further illumination patterns for further image recordings are determined in a manner dependent on the region properties of the individual light origin region.

In this configuration, the determination of the light origin region is a preliminary examination in order to implement, for example, an optimum stripe width (period) and stripe direction for a further inspection of the test specimen using phase shifting methods as described in DE 10 2007 063 529 A1 cited in the introduction. In particular, in preferred exemplary embodiments of this configuration, a local surface inclination of the surface point considered is determined on the basis of the further illumination patterns and image recordings. The configuration allows a faster and targeted selection of the optimum stripe width and stripe direction for such an exemplary embodiment.

In a further configuration, a multiplicity of individual light origin regions are determined for a multiplicity of pixels.

This configuration extends the above-described method to a multiplicity of pixels. The configuration enables a location-dependent characterization of a test specimen surface, that is, a characterization of the test specimen surface at a multiplicity of surface points arranged in a distributed fashion, in a simple manner.

In a further configuration, the illumination device has a matrix of at least 10×10 light sources. In this case, it is particularly preferred if the individual light sources are individually driveable. In one preferred exemplary embodiment, the individual light sources are LEDs that form a corresponding matrix. In other exemplary embodiments, the illumination device can be an LCD monitor or a light projector, in which the illumination patterns are generated with the aid of a suitable mask in the light beam.

An illumination device having a matrix of at least 10×10 light sources enables a very variable and individual realization of the novel method for a multiplicity of different test specimens. Furthermore, the individual light origin regions for a multiplicity of surface points can be determined simply and rapidly.

In a further configuration, the light sources of the illumination device form a tunnel-like sheathing surface that surrounds the surface.

This configuration enables a very flexible, individual and fast inspection of an unknown, or at least largely unknown test specimen according to the novel method. By virtue of the tunnel-like sheathing surface, a large solid angle range is covered with light sources, which contributes to detecting the individual light origin region as completely as possible.

In a further configuration, a first and at least one second series of different illumination patterns are generated, wherein the illumination patterns of the first and second series are identical, but are generated at different distances with respect to the surface.

This configuration makes it possible, in a simple manner, to additionally determine 3D coordinates of the surface points considered, since the individual light origin regions from the first and second series have to be related on account of the central perspective of the defined pixel in the manner of a projection. This configuration thus enables a comprehensive characterization of a test specimen with regard to shape features and surface properties.

It goes without saying that the features mentioned above and those yet to be explained below can be used not only in the combination respectively specified, but also in other combinations or by themselves, without departing from the scope of the present invention.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
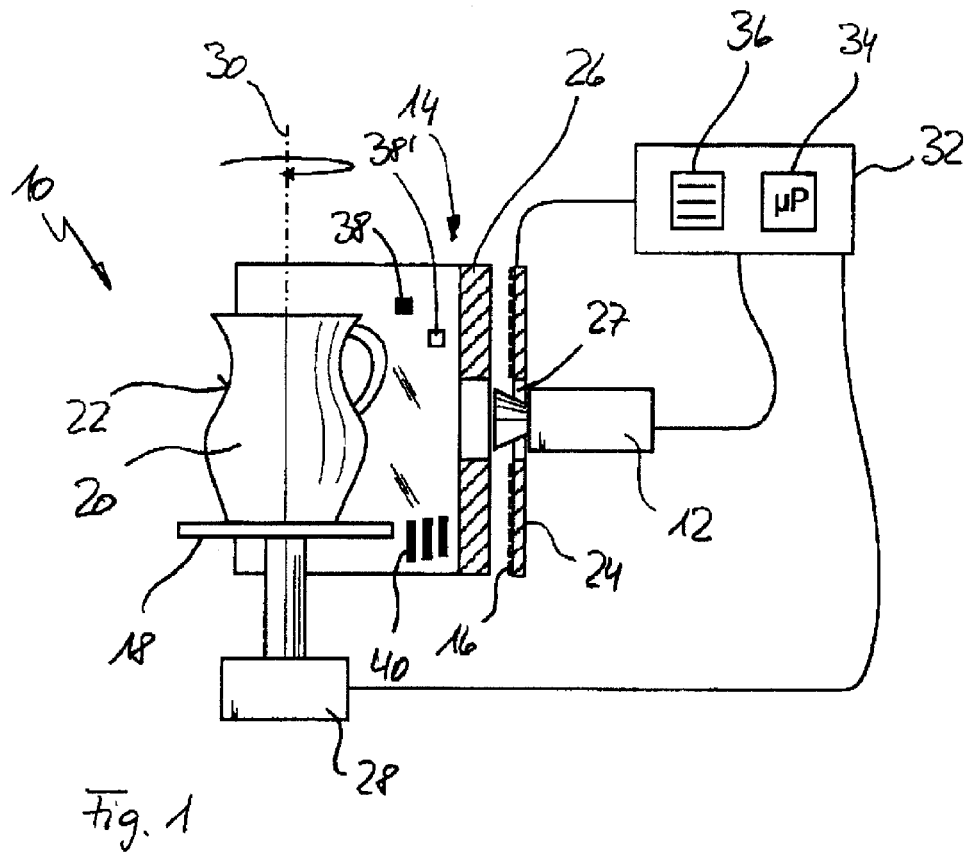
FIG. 1 shows a first exemplary embodiment of the novel apparatus in a simplified, partly sectional side view.
Figure 2:
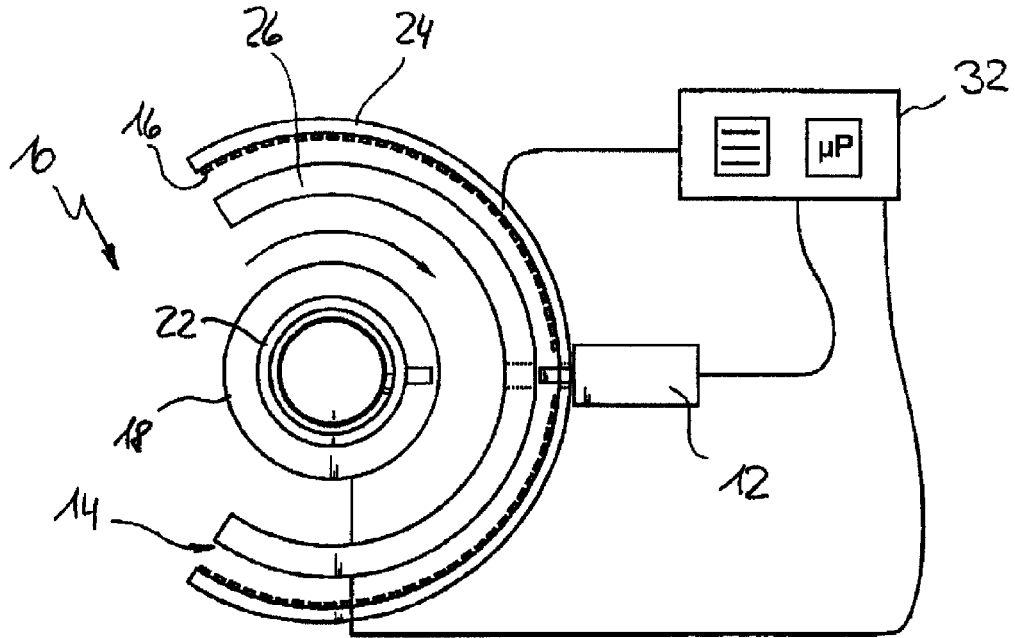
FIG. 2 shows the exemplary embodiment from FIG. 1 in a view from above.

In FIGS. 1 and 2, a first exemplary embodiment of the novel apparatus is designated in its entirety by the reference numeral 10. The apparatus 10 has a camera 12, an illumination device 14 having a multiplicity of light sources 16 and a workpiece receptacle 18. In the exemplary embodiment illustrated here, the light sources 16 are individually driveable LEDs, although in some exemplary embodiments a plurality of small LEDs can be combined to form a larger "light node" in order to generate a higher quantity of light per light source. The LEDs interconnected to form a "light node" are understood here as a light source within the meaning of the present invention.

A test specimen 20 having an at least partly reflective surface 22 is arranged on the workpiece receptacle 18. In the exemplary embodiment illustrated, the test specimen is a jug having a lacquered, largely lustrous surface 22.

A cylindrical shell is designated by the reference numeral 24, a multiplicity of LEDs being arranged in a matrix-like manner on the inner lateral surface of the cylindrical shell. The multiplicity of LEDs form a "wallpaper" of light sources on the inner side of the cylindrical shell 24. Arranged concentrically in the interior of the cylindrical shell 24 is a light-transmissive ground-glass screen 26, through which the light from the LEDs can be incident on the test specimen 20. In preferred exemplary embodiments, the ground-glass screen 26 is a satinized Plexiglass plate or a comparable semitransparent ground-glass screen. It has the effect that the individual light sources behind the ground-glass screen 26 blur, and thus contributes to the fact that illumination patterns having largely continuous brightness profiles (without "steps") can be generated on the ground-glass screen 26. Both the cylindrical shell 24 and the ground-glass screen 26 have approximately centrally a hole 27, through which the camera 12 can look at the surface 22 of the test specimen 20.

An electric drive is designated by the reference number 28, with the aid of which electric drive the workpiece receptacle 18 can be rotated about a vertical axis 30. This makes it possible to inspect the rear side of the test specimen 20 facing away from the camera 12. Alternatively, a further camera (not illustrated here) could be arranged on the rear side of the test specimen for this purpose.

An evaluation and control unit is designated by the reference numeral 32. In preferred exemplary embodiments, this unit is a PC having a processor 34 and a memory 36. Firstly, a computer program (not illustrated here) designed for carrying out the novel method with all method steps is stored in the memory. Furthermore, the memory 36 serves for storing images recorded by the camera 12.

A first illumination pattern is represented at the reference numeral 38. The illumination pattern 38 arises if an individual light source 16 is switched on, while all of the other light sources 16 are switched off. A further illumination pattern of this type is represented at the reference numeral 38', this pattern arising if a different light source 16 is individually switched on. The illumination patterns (38, 38') here form a series of different illumination patterns within the meaning of the novel method.

A further illumination pattern is indicated as an excerpt at the reference numeral 40. The illumination pattern 40 consists of a multiplicity of bright and dark stripes which form a preferably sinusoidal intensity profile transversely with respect to the stripe direction. In preferred exemplary embodiments, the further illumination pattern 40 serves for determining test specimen properties including the local inclinations of the surface points of the test specimen 20, as described in DE 10 2007 063 529 A1 cited in the introduction. Advantageously, the illumination pattern 40 is selected in a manner dependent on region properties of an individual light origin region, wherein this last is determined (implemented) with the aid of the illumination patterns (38, 38') according to the novel method.

As an alternative thereto, a stripe pattern of the type indicated at reference numeral 40 could also be used to determine individual light origin regions within the meaning of the novel method. In these cases, the illumination pattern is particularly advantageously a one-dimensional or two-dimensional chirp pattern (areal sinusoidal pattern having a linearly increasing frequency in one direction or in a plurality of directions) or a pseudo random noise pattern with a peak-like autocorrelation function.

In the following explanation of one preferred exemplary embodiment of the novel method, identical reference signs designate the same elements as above.

Figure 3:
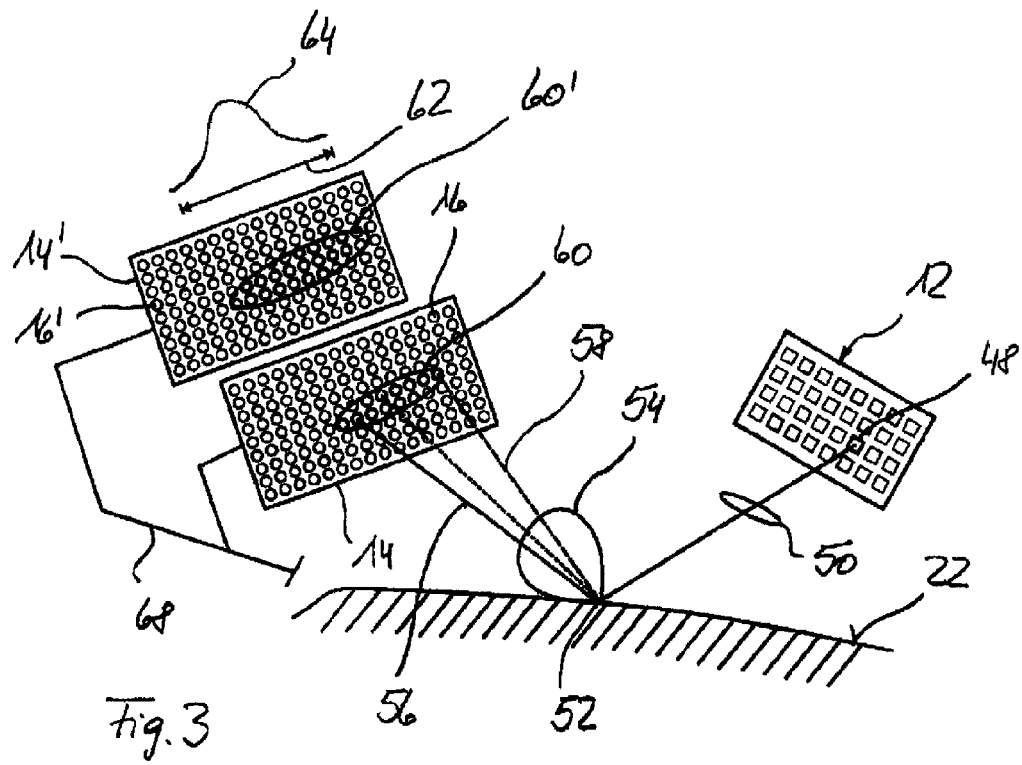
FIG. 3 shows a schematic illustration for elucidating one preferred exemplary embodiment of the novel method; and, FIG. 4 shows a further exemplary embodiment of the novel apparatus and of the novel method.

FIG. 3 illustrates the camera 12 in a simplified fashion with a matrix of pixels and an optical unit 50. The use of a matrix camera is preferred. In principle, however, a line camera could also be used, particularly if the test specimen 20 is arranged on a rotatable workpiece receptacle 18, as is illustrated in FIGS. 1 and 2. Furthermore, in other exemplary embodiments, the novel apparatus can also be realized with a translationally moving test specimen 20, for instance if the test specimen 20 is led past the camera 12 on a conveyor belt. In this case, too, the camera 12 could be realized as a line camera.

A surface point on the surface 22 of the test specimen 20 is designated by the reference numeral 52. The surface point 52 has reflection and scattering properties which can be represented technically by a so-called scattering lobe 54. The scattering lobe 54 indicates in what directions and with what intensity a light beam impinging on the surface point 52 is scattered. In the case of an ideal so-called Lambert emitter, the scattering lobe is spherical. This means that such an emitter scatters incident light uniformly in all spatial directions.

By way of example, two light beams that emerge from two different light sources 16 of the illumination device 14 are designated by the reference numerals (56, 58). Since the scattering properties of the surface point 52 are also effective in the opposite direction, each light beam (56, 58) generates an individual light contribution on the pixel 48 under consideration. For clarification, all light sources 16 that generate an individual light contribution on the pixel 48 are illustrated in bold in FIG. 3. The set of all light sources 16 which generate a light contribution on the pixel 48 defines an individual light origin region, which is designated by the reference numeral 60 in FIG. 3. The individual light origin region 60 is largely elliptical in the case illustrated, and it has an extent indicated by way of example at the reference numeral 62 for the major axis of the ellipse. Furthermore, the light origin region 60 has an intensity distribution along the major axis, the intensity distribution being indicated by way of example at the reference numeral 64. The region properties of the light origin region 60, in particular the extent, the shape, the orientation (in this case of the ellipse) in the plane spanned by the light sources 16, symmetries present and the intensity distribution, characterize the scattering lobe 54 of the surface point 52. Accordingly, the individual light origin region 60 for the pixel 48, in the preferred exemplary embodiments of the novel method, is determined on the basis of the images recorded by the camera 12. The region properties of the light origin region 60, such as shape, extent, symmetry, orientation, et cetera, are subsequently determined in order to determine the scattering characteristic of the surface point 52. In preferred exemplary embodiments, an illumination pattern 40 having an optimum stripe direction and an optimum stripe width (period) for subsequent inspection of the test specimen 20 is determined in a manner dependent on the identified region properties of the light origin region 60.

In the preferred exemplary embodiments, individual light origin regions 60 are determined for a multiplicity of pixels 48 of the camera 12. Since each pixel 48 sees "its" individual light origin region 60 via a different surface point 52, a location-dependent scattering characteristic of the test specimen surface 22 is obtained in this way.

FIG. 3 illustrates a further illumination device 14', which is arranged at a larger radial distance from the surface point 52 than the first illumination device 14. For the rest, the further illumination device 14' is identical to the first illumination device 14. The larger distance of the further illumination device 14' can be realized, for example, by virtue of the fact that the illumination device 14 can be displaced on a rail 68. One particularly preferred example for realizing the illumination devices (14, 14') is explained further below with reference to FIG. 4.

Since the light sources 16' of the illumination device 14' reach the camera pixel 48 via the same scattering lobe 54 as the light sources 16 of the illuminating device 14, the individual light origin region 60' on the illumination device 14' is a "copy" of the light origin region 60 that is magnified on account of the central projection (proceeding from the camera pixel 48 or the surface point 52). Therefore, it is possible to determine the 3D coordinates of the surface point 52 in a coordinate system spanned by the camera pixel 48 and the illumination devices (14, 14') according to the laws of central projection. In preferred exemplary embodiments of the novel method, the 3D coordinates for a multiplicity of surface points 52 are determined according to this variant of the novel method in order, in addition to the scattering properties of the surface 22, also to determine the surface shape of the test specimen 20.

Figure 4:
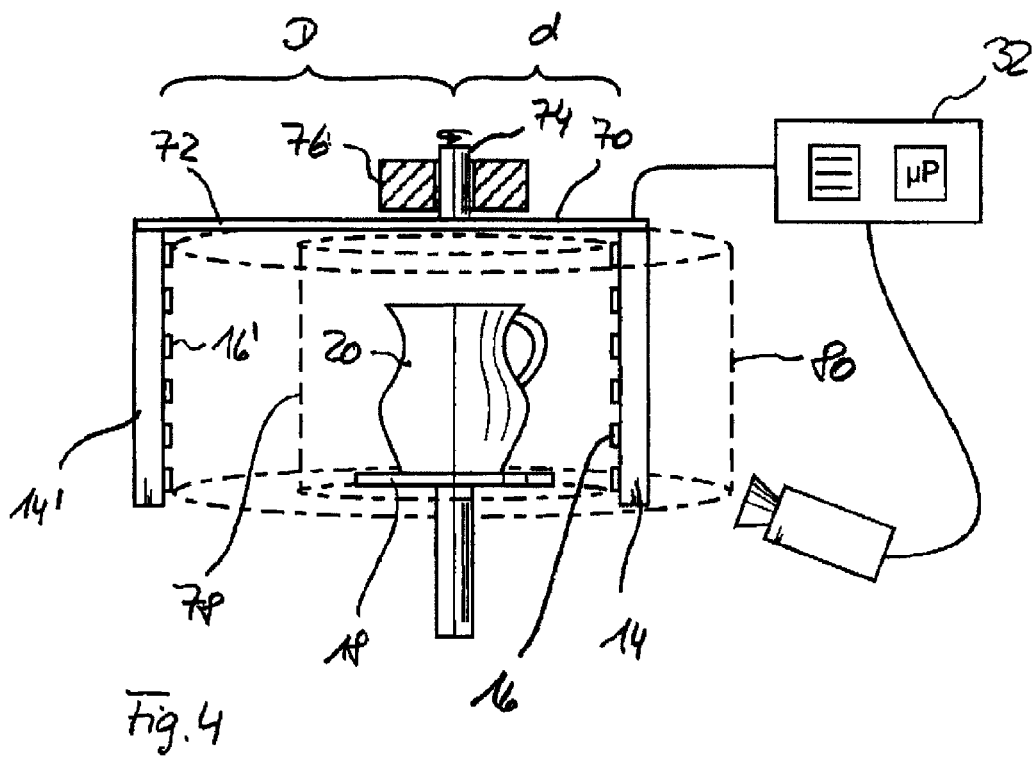

One particularly preferred exemplary embodiment for the practical realization of this variant of the novel method is illustrated in FIG. 4. Identical reference signs designate the same elements as above.

In FIG. 4, the first illumination device 14 and the second illumination device 14' are fixed to the free ends of an eccentrically mounted carrying arm (70, 72). A first arm part 70 carries the first illumination device 14, a second arm part 72 carries the second illumination device 14'. The arm parts (70, 72) are fixed to a shaft 74 and extend radially outward from the shaft 74. In the preferred exemplary embodiment, the first illumination device 14 and the second illumination device 14' are diametrically opposite each other in order to provide weight compensation during the rotation of the shaft 74. If appropriate, compensating weights can be arranged on the short arm part 70 and/or the first illumination device 14. The shaft 74 is mounted rotatably in a bearing 76. As can be discerned in FIG. 4, the distance (d) between the rotation mid point of the shaft 74 and the illumination device 14 is less than the distance D between the rotation mid point of the shaft 74 and the further illumination device 14'.

In the preferred exemplary embodiment, the illumination devices (14, 14') are embodied largely in rod-shaped fashion, wherein the light sources (16, 16') in each case form a line or a narrow matrix (having a long extent parallel to the axis of rotation and a short extent tangential to the axis of rotation) of light sources, which extends approximately parallel to the axis of rotation of the shaft 74. On account of the rotational movement of the shaft 74, the light sources 16 of the first illumination device 14 sweep over a first lateral cylindrical surface 78. The light sources 16' of the second illumination device 14' sweep over a second lateral cylindrical surface 80. The two lateral cylindrical surfaces (78, 80) are concentric with respect to the axis of rotation of the shaft 74 and concentric with respect to each other. On account of the rotational movement of the shaft 74 it suffices if the illumination devices (14, 14') in each case occupy only a small section of the lateral cylindrical surface (78, 80). It may be advantageous if the "light lines" of the illumination devices (14, 14') are inclined in the direction of rotation or counter to the direction of rotation, that is to say are not exactly parallel to the axis of rotation. One particularly advantageous variant is one in which the "light lines" of the illumination devices (14, 14') are inclined differently in relation to the direction of rotation, that is to say that the light line of the illumination devices 14 is inclined in the direction of rotation and the light line of the illumination devices 14' is inclined counter to the direction of rotation (or vice versa). In this case, the two light lines of the illumination devices (14, 14') are parallel to one another. This variant makes it possible to generate advantageous bright-dark patterns with obliquely extending stripes very simply and rapidly. In some exemplary embodiments, the light lines of the illumination devices (14, 14') are inclined at one of the following angles: approximately 30°, approximately 45° or approximately 60°.

The recording of all required images can be realized with the illumination device 14 and/or 14' in a very simple and rapid manner by a procedure in which the arm part 70 and/or 72 rotates once around the workpiece (or the workpiece surface of interest) and, at defined rotational angle positions of the arm part, the individual light sources of the light line are individually switched on in order. The defined rotational angle positions can be separated from one another in each case by 1°, 3°, 5° or 10°, for example, depending on what resolution of the light origin regions is desired. If the individual light sources are switched through rapidly enough, a quasi-continuous circulating movement of the arm part is also possible.

It is understood that the foregoing description is that of the preferred embodiments of the invention and that various changes and modifications may be made thereto without departing from the spirit and scope of the invention as defined in the appended claims.

What is claimed is:

1. A method for optically inspecting a test specimen having an at least partly reflective surface, the method comprising:
   providing a camera having a number of pixels;
   providing an illumination device having a multiplicity of spatially distributed light sources;
   positioning the test specimen relative to the illumination device and the camera, such that light from the light sources is reflected via the surface to the camera when the light source is switched on;
   generating a series of two or more mutually different illumination patterns on the surface, wherein two or more light sources are switched on in the course of generating the series,
   recording a series of images of the surface with respective ones of the illumination patterns, and
   determining properties of the test specimen in a manner dependent on the images;
   wherein an individual light origin region is determined on the basis of the images recorded by the camera for at least one pixel, the region representing a spatial distribution of individual light contributions generated by the light sources via the surface on the at least one pixel and wherein the properties of the test specimen are determined on the basis of the individual light origin region.

2. The method according to claim 1, further comprising switching on each light source whose light is reflected via the surface to the camera once.

3. The method according to claim 1, further comprising switching on each light source whose light is reflected via the surface to the camera individually.

4. The method according to claim 1, wherein in the course of the generating the series a plurality of light sources are switched on simultaneously to generate a multiplicity of spatially extended illumination patterns and wherein the individual light contributions of the light sources used are calculated on the basis of the multiplicity of spatially extended illumination patterns.

5. The method according to claim 1, wherein the light sources are each digitally switched on or off in the course of the generating the series.

6. The method according to claim 1, wherein region properties of the individual light origin region are identified and wherein the properties of the test specimen are determined on the basis of region properties of the individual light origin region.

7. The method according to claim 6, wherein the identified region properties are selected from the group of region properties consisting of a shape of the individual light origin region, an extent of the individual light origin region, a symmetry of the individual light origin region, an orientation of the individual light origin region, and an intensity distribution within the individual light origin region.

8. The method according to claim 6, wherein a predetermined number of further illumination patterns for further image recordings are determined in a manner dependent on the region properties of the individual light origin region.

9. The method according to claim 1, wherein a multiplicity of individual light origin regions are determined for a multiplicity of pixels.

10. The method according to claim 1, wherein the illumination device comprises a matrix of at least 10×10 light sources.

11. The method according to claim 1, wherein the light sources of the illumination device form a tunnel-like sheathing surface that surrounds the surface at least partially.

12. The method according to claim 1, wherein a first and at least one second series of different illumination patterns are generated, wherein the illumination patterns of the first and second series are identical, but are generated at different distances with respect to the surface.

13. An apparatus for optically inspecting a test specimen having an at least partly reflective surface, the apparatus comprising:
   a camera having a number of pixels;
   an illumination device having a multiplicity of spatially distributed light sources;
   a workpiece receptacle for positioning the test specimen relative to the illumination device and the camera so as to cause light from the light sources to be reflected via the surface to the camera when the light source is switched on;
   a control unit for generating a series of two or more mutually different illumination patterns on the surface, wherein two or more light sources are switched on in the course of generating the series, and for recording a series of images of the surface with respective ones of the illumination patterns;
   an evaluation unit for determining properties of the test specimen in a manner dependent on the images; and,
   the evaluation unit being configured to determine an individual light origin region on the basis of the images recorded by the camera for at least one pixel, the region representing a spatial distribution of individual light contributions generated by the light sources via the surface on the at least one pixel and the evaluation unit being further configured to determine properties of the test specimen on the basis of the individual light origin region.

* * * * *